United States Patent [19]

Rand

[11] Patent Number: 5,516,922
[45] Date of Patent: May 14, 1996

[54] PROCESS FOR THE PREPARATION OF 10(2-PROPYNYL)ESTR-4-ENE-3,17-DIONE

[75] Inventor: Cynthia L. Rand, Sanford, Mich.

[73] Assignee: Merrell Pharmaceuticals Inc., Cincinnati, Ohio

[21] Appl. No.: 468,886

[22] Filed: Jun. 6, 1995

Related U.S. Application Data

[63] Continuation of Ser. No. 359,708, Dec. 20, 1994, abandoned, which is a continuation of Ser. No. 114,802, Aug. 31, 1993, abandoned, which is a continuation of Ser. No. 987,985, Dec. 9, 1992, abandoned, which is a continuation of Ser. No. 692,321, May 2, 1991, abandoned, which is a continuation-in-part of Ser. No. 530,674, May 30, 1990, abandoned.

[51] Int. Cl.$^6$ .......................................................... C07J 1/00
[52] U.S. Cl. ............................................ 552/632; 552/630
[58] Field of Search ...................................... 552/632, 630

[56] References Cited

FOREIGN PATENT DOCUMENTS

| 3438484 | 4/1986 | Germany. |
|---|---|---|
| WO9002781 | 3/1990 | WIPO. |

OTHER PUBLICATIONS

P. J. Bednarski et al., J. Med. Chem., 32, 203–263 1989.
Lipshutz et al. Tetrahedron letters, 28, No. 9 pp. 945–948, 1987.
P. J. Bednarski, PhD. Thesis (University of Washington), pp. 61–63, 78, 79, 96–98 (1986).
E. Erdik, *Tetrahedron*, 40, 641–657 (1984).
B. H. Lipshutz et al., *Tetrahedron*, 40, 5005–5038 (1984).
G. H. Posner, "Organic Reactions" vol. 22, pp. 253–255, 287–289 and 389–393 (1975).
*Chemical Abstracts*, Eleventh Collective Index, 1982–1986 Formula Index, p. 19059F.
*Chemical Abstracts*, 105, 115283y (1986).
B. H. Lipshutz et al, *Tetrahedron Letters*, 25, No. 52, 5959–5962 (1984).
B. H. Lipshutz et al., J. Org. Chem., 49, 3938–3942, (1984).
B. H. Lipshutz et al., J. Org. Chem., 49, 3928–3938, (1984).
B. H. Lipshutz et al., Tetrahedron Letters, 28, 945–948, (1987).
Bednarski, et al., J. of Med. Chem. vol. 32(1), p. 203 (1989).
P. J. Bednarski, PhD. Thesis (University of Washington), pp. 61–63, 78, 79, 96–98 (1986).
E. Erdik, Tetrahedron, 40, 641–657 (1984).
B. H. Lipshutz et al., Tetrahedron, 40, 5005–5038 (1984).
G. H. Posner, Organic Reactions, vol. 22, pp. 253–255, 287–289 and 389–393 (1974).
Chemical Abstracts, Eleventh Collective Index, 1982–1986 Formula Index, p. 19059F. 1986.
B. H. Lipshutz et al, J. Org. Chem., 49, 3938–3942 (1984).
B. H. Lipshutz et al, J. Org. Chem., 49, 3928–3938 (1984).
B. H. Lipshutz et al, Tetrahedron Letters, vol. 28, No. 9, pp. 945–948, (1987).
S. W. Smith, et al., J. of the Amer. Chem. Soc., vol. 90, No. 5, pp. 1249–1253, (1968).

*Primary Examiner*—Mukund J. Shah
*Assistant Examiner*—Pavanaram K. Sripada
*Attorney, Agent, or Firm*—Ruth E. Homan

[57] ABSTRACT

This invention relates to a process for the preparation of 10-(2-propynyl)-estr-4-ene-3,17-dione, whereby this compound is synthesized utilizing ketals prepared from the addition of 2,2-dimethyl-1,3-propanediol to the starting compound, 19-norandrost-5(10)-ene-3,17-dione (NAD). A new process for the addition of the propynyl group to steroid epoxides by means of higher order cuprates is also described herein.

2 Claims, No Drawings

PROCESS FOR THE PREPARATION OF 10(2-PROPYNYL)ESTR-4-ENE-3,17-DIONE

This is a continuation of application Ser. No. 08/359,708 filed Dec. 20, 1994, aband. which is a continuation of application Ser. No. 08/114,802, filed Aug. 31, 1993, now abandoned, which is a continuation of application Ser. No. 07/987,985, filed Dec. 9, 1992, now abandoned, which is a continuation of application Ser. No. 07/692,321, filed May 2, 1991, now abandoned, which is a continuation-in-part of application Ser. No. 07/530,674, filed May 30, 1990, now abandoned, which is herein incorporated by reference.

BACKGROUND OF THE INVENTION 10-(2-Propynyl)-estr-4-ene-3,17-dione, described in U.S. Pat. No. 4,322,416, is a useful potent and selective aromatase inhibitor. In that patent, this compound is prepared by a multi-step procedure which comprises reacting the chloroethenyl compound, 3,3,17,17-bis(ethylenedioxy)-10-(3-chloro-prop-2-enyl)estr-5-ene, with a strong base in an inert solvent to yield the corresponding 10-(2-propynyl) compound, followed by treatment with acid to remove the protecting groups at the 3- and 17- positions, with shifting of any 5-unsaturation to the 4-position. This method of preparation is long, involves the use of mercury and lead, and requires chromatography. Although each step in this process proceeds in over 70% yield, the overall yield is only 13%.

More recently, Bednarski et al., *J. Med. Chem.*, Vol 32, 203 No. 1 (1989), described a process for the preparation of 10-(2-propynyl)-estr-4-ene-3,17-dione. That process utilizes the preparation of ethylene ketal intermediates, but these and subsequent intermediates tend to oil out of recrystallization media and are difficult to handle in a process. In addition, although Bednarski did not recognize this fact, in the preparation of the initial bisketal, isomerization of the 5(10)-double bond occurs under the conditions described and the product obtained is actually a mixture of the product with a significant amount of an isomeric compound.

SUMMARY OF THE INVENTION

The present invention is directed to a new process for the preparation of 10-(2-propynyl)estr-4-ene-3,17-dione from 19-norandrost-5(10)-ene-3,17-dione. 10-(2-Propynyl)estr-4-ene-3,17-dione has the following formula.

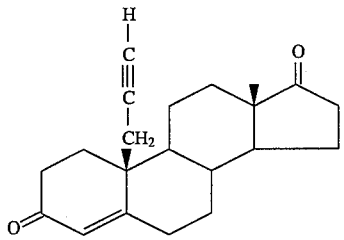

The new process is simpler than the earlier procedures and gives the desired product in an improved overall yield and without isomerization of the double bond in the initial starting material. It utilizes ketals from 2,2-dimethyl-1,3-propanediol in the preparation of intermediates, which subsequently yield crystalline solids throughout the reaction sequence. More particularly, the present application is directed to a new process for the preparation of 10-(2-propynyl)-estr-4-ene-3,17-dione (see Formula 1, above) which comprises:

(a) reacting 19-norandrost-5(10)-ene-3,17-dione, 2,2-dimethyl-1,3-propanediol, and trimethyl or triethyl orthoformate in solvent at a temperature of from −10° C. to +10° C., in the presence of a strong acid for a period of from 3 to 72 hours, to yield the bisgemdimethyldioxan, 3,3,17,17-bis(2,2-dimethyltrimethylenedioxy)-19-norandrost-5(10)-ene, (b) reacting 3,3,17,17-bis(2,2-dimethyltrimethylenedioxy)-19-norandrost-5(10)-ene with N-bromosuccinimide and aqueous buffer to yield the bromohydrin, and then reacting the bromohydrin with a strong base to yield the α-epoxide, (5α,10α)-5,10-epoxy-3,3,17,17-bis(2,2-dimethyltrimethylene-dioxy)-19-norandrostane, (c) reacting (5α,10α)-5,10-epoxy-3,3,17,17-bis(2,2-dimethyltrimethylenedioxy)-19-norandrostane with a trialkylsilyl protected 2-propynyl copper salt in diethylether or tetrahydrofuran to yield the bisgemdimethyl ketal, 10-[3-(trimethylsilyl)-2-propynyl]-3,3,17,17-bis(2,2-dimethyltrimethylenedioxy)-19-norandrostan-5-ol, and (d) reacting 10-[3-(trialkylsilyl)-2-propynyl]-3,3,17,17-bis(2,2-dimethyltrimethylenedioxy)-19-norandrostan-5-ol with deblocking reagents to yield 10-(2-propynyl)estr-4-ene-3,17-dione.

The alkyl groups referred to above contain 1 to 4 carbon atoms and can be exemplified by methyl, ethyl, propyl, n-butyl and t-butyl.

The present invention is further directed to an improvement in a process for the preparation of a δ-unsaturated alkanol by the reaction of an epoxide with a (2-propynyl or 2-propenyl)organometallic compound wherein the organometallic compound is a higher order cuprate and, particularly, a catalytic amount of the cuprate. A specific exemplification of the general chemical reaction involved in this improvement is set forth in Step (c) above.

DETAILED DESCRIPTION OF THE INVENTION

The present procedure avoids the difficult modification of the neopentyl 19-alkyl group present in most steroid starting materials. Typically, in the synthesis of 19-substituted steroids, the alkyl group is converted to a 19-hydroxy group which can be nucleophilically substituted via a Sn1 pathway. In the case of lithium acetylide, this leads to several competing pathways. Alternatively, to remove the limitations of nucleophilic substitution at a neopentyl system, the 19-hydroxy group can be oxidized to an aldehyde so that addition reactions can occur. Acetylide addition to the aldehyde proceeds smoothly, but the resulting alkanol is deoxygenated with some difficulty. Alternatively, removal of the neopentyl 19-alkyl group during the synthesis allows substitution at the 10-position during the reaction sequence which leads to a complex synthesis. Thus, the use of 19-norandrost-5(10)-ene-3,17-dione (NAD) considerably simplifies the synthesis of 10-(2-propynyl)estr-4-ene-3,17-dione. Specifically, the process of this invention is represented by Scheme 1, following:

Scheme 1

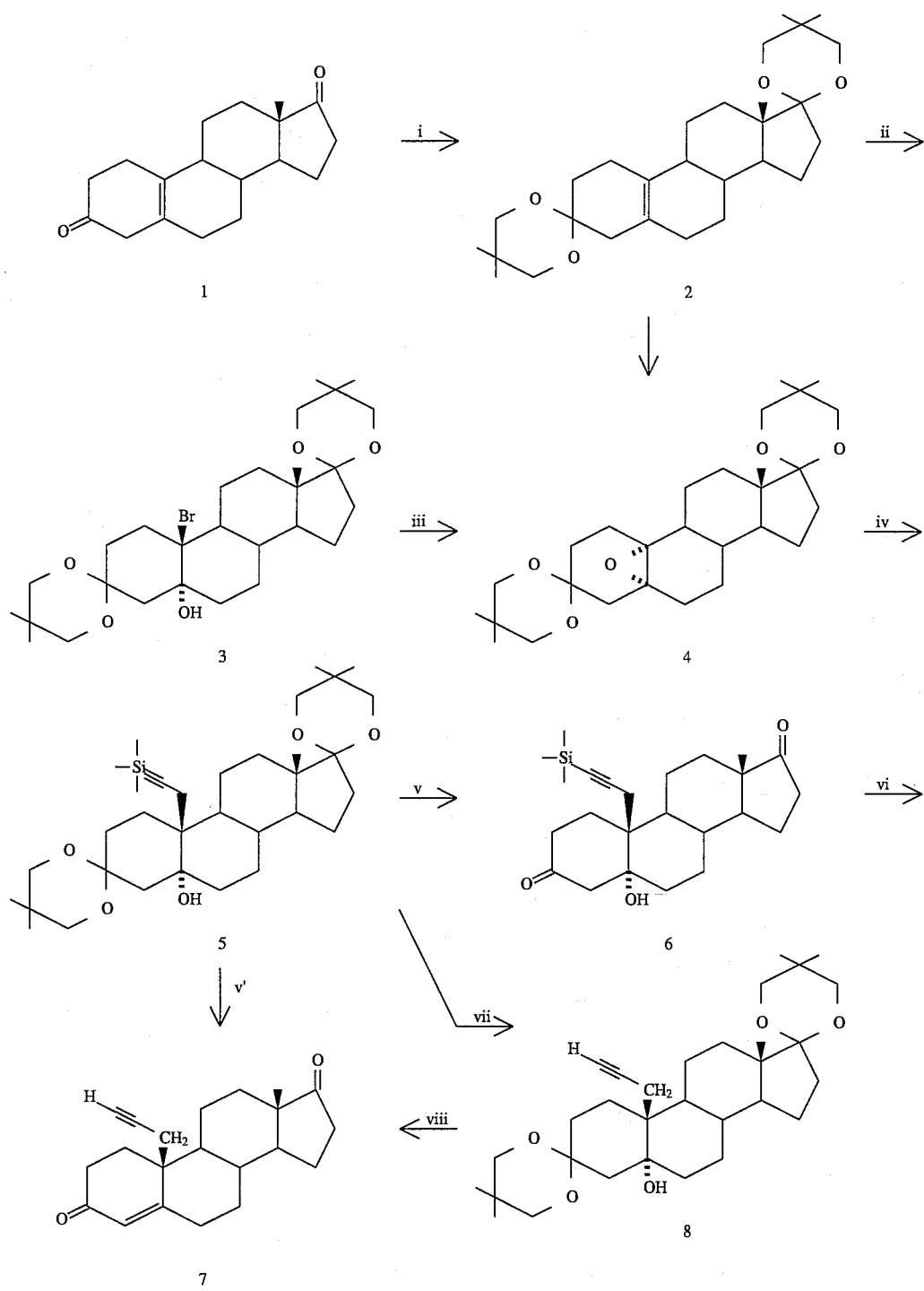

As illustrated in the previous procedure, in step (i), the commercially available compound 19-norandrost-5(10)-ene-3,17-dione (NAD) (1), 2,2-dimethyl-1,3-propanediol, and triethyl orthoformate is mixed in a solvent such as toluene, methanol, or more preferably, ethanol, and cooled to a temperature of from −10° C. to +10° C., or more preferably, from 0° C. to +4° C. To this mixture, a catalytic quantity of a strong acid, such as, for example, p-toluenesulfonic acid monohydrate, i.e., 0.36 to 10 mol % of, or more preferably, 0.90 mol %, is added. The resulting stirred solution is maintained at a temperature of from −10° C. to +10° C., or more preferably, from 0° C. to +4° C., for a period of from 3 to 72 hours, or more preferably, 24 hours. The resulting bisgemdimethyldioxan (2), if prepared in toluene, is then readily recrystallized from methanol or ethanol in 80–82% yield with a purity of at least 95%. If the ketalization is carried out in methanol or ethanol, the product crystallizes from solution as it forms. After quenching the acid catalyst with organic base, e.g. triethylamine, the product (2) can be isolated by simple filtration in 75–85% yield with a purity of 95% or greater. Thus, preparation of the bisgemdimethyldioxan (2) in an alcohol solvent is unique because it avoids isomerization of the 5(10)-double bond and yields crystalline solid. On the other hand, in refluxing toluene, significant amounts of the A5-compound are formed so that a mixture of isomers is obtained and the resulting mixture of compounds is an oil and cannot be used in the synthesis described below without introduction of many side reactions and a significant loss of material because of the presence of the undesired isomer.

The bromohydrin (3), step (ii), is synthesized by addition of at least one equivalent of N-bromosuccinimide (NBS) to an aqueous solution of the bisgemdimethyldioxan (2) in DMF or THF, buffered preferably with no more than one equivalent of magnesium oxide. Other buffers, such as, for example, calcium carbonate, calcium oxide, magnesium carbonate, and $KH_2PO_4$ may also be used. If run in DMF, the reaction is simply worked up by addition of water, filtration of the resulting solid, and extraction with ethyl acetate to yield pure dry bromohydrin. If run in aqueous THF, the bromohydrin can be used without isolation as discussed below.

In step (iii), the α-epoxide (4) is formed via the bromohydrin (3) and subsequent cyclization with a base, such as, for example, potassium tert-butoxide or potassium hydroxide. Preferably, epoxidation is readily achieved via addition of a strong base, such as, for example, by using 1.5 to 2.5 equivalents of commercial potassium tert-butoxide, potassium hydroxide, benzyltrimethylammonium hydroxide, NaOMe, sodium hydroxide, or Dowex® resin in strong base or hydroxide form in either THF or DMF. If the bromohydrin was formed in $THF/H_2O$, potassium hydroxide may be added directly to that mixture to effect epoxide formation. The resulting solid α-epoxide (4) is recrystallized from methanol, acetone, or hexane to yield a stable crystalline solid.

In step (iv), introduction of the $C_3H_4$ fragment or propargylic group is achieved by the use of a trialkylsilyl-protected 2-propynyl copper salt, such as, for example, a propargylic cuprate. The trialkylsilyl group allows formation of the δ anion and also prevents allene formation, thus giving exclusively the desired terminal acetylene. Formation of the cuprate is achieved by deprotonation of 1-(trialkylsilyl)propyne with n-BuLi at about 0° C. and its addition to a copper(I) salt, such as, for example, copper(1) bromide, at 15° C in the presence of dimethylsulfide. The resulting cuprate is reacted with epoxide (4) and the reaction is quenched and subsequently filtered through a bed of silica gel, then recrystallized from isopropanol to yield, for example, the bisgemdimethyl ketal, 10-[3-(trimethylsilyl)-2-propynyl]-3,17-bis(2,2-dimethyltrimethylenedioxy)androstan-5-ol (5).

A preferred procedure for the formation of the bisgemdimethyl ketal (5) involves the addition of three equivalents of a "higher order" copper reagent ("higher order" cuprate), such as, for example, dilithium cyano bis[3-(trimethylsilyl)-2-propynyl]cuprate (9a), which may be obtained from copper(I) cyanide and two equivalents of lithium 1-(trimethylsilyl)propyne in diethyl ether or tetrahydrofuran. Alternatively, a related cuprate may be prepared by using copper(I) bromide instead of copper(I) cyanide. This cuprate is reacted with the epoxide and the reaction proceeds in one pot. Quenching the reaction mixture with about 10% $NH_4OH$/saturated $NH_4Cl$ and filtration through celite yields a colorless, clear solution, which is simply evaporated to yield, for example, the pure bisgemdimethyl ketal, 10-[3-(trimethylsilyl)-2-propynyl]-3,17-bis(4,4-gemdimethyldioxan)androstan-5-ol (5) in quantitative yield without the need of further purification. This method eliminates the use of dimethyl sulfide and simplifies the work up to an easy wash and evaporation.

A more preferred procedure to form the bisgemdimethyl ketal (5) involves the use of mixed higher order cuprates derived from cuprates which have two organic substituents, one of which is preferably 2-thienyl. Examples of such higher cuprates are dilithium [3-(trimethylsilyl)-2-propynyl] methyl-2-thienylcuprate (9b) and dilithium [3-(trimethylsilyl)-2-propynyl]di-2-thienylcuprate (9c). Lithium methyl-2-thienylcuprate or lithium di-2-thienylcuprate serve as the starting materials for the preparation of the indicated mixed higher order cuprates. This procedure offers a reagent which, when reacted with epoxides such as (4), selectively delivers a propargylic nucleophile to give products such as the bisgemdimethyl ketal (5). These reagents, (9b) and (9c), offer unique advantages such as high selectivity in the transfer of the propargylic functionality with more efficient use of the propargylic groups in the organometallic reagents and with no detectable evidence for transfer of the methyl group. Further, these reagents selectively open the epoxide without evidence for allylic alcohol formation due to beta-proton abstraction. These reagents also have a higher reactivity than the homocuprate (9a) described above and thus allow for a significant reduction in the total reaction time or in the amount of copper reagent used. These copper reagents may also be used catalytically (5–30 mol %, preferably 10 mol %) in this reaction. That is, the copper reactant (i.e., lithium methyl-2-thienylcuprate or lithium di-2-thienylcuprate) used to prepare the higher order cuprate, can be used in catalytic amounts. Use of catalytic quantities of copper reagents in this way is very advantageous in that it significantly reduces the amount of copper waste produced by the reaction. Such a catalytic reaction, with highly substituted epoxides, has not been previously described.

Alternatively, the bisgemdimethyl ketal (5) may be prepared from the bisgemdimethyldioxan (2) without any change in solvent or without isolation of intermediates. This process involves a modified preparation of the bromohydrin (3) from the bisgemdimethyldioxan (2) which offers advantages such as a homogenous reaction medium, a close to stoichiometric use of N-bromosuccinimide, and a rapid reaction between all reagents at moderate temperatures. General process advantages include the substitution of a homogenous buffer such as $KH_2PO_4$ for MgO, which simplifies the isolation of the bromohydrin (3). The choice of a non-nucleophilic aprotic solvent, such as THF, that is compatible with subsequent steps, also allows direct conversion of the epoxide (4) to the bisgemdimethyl ketal (5) without solvent exchanges or isolation, if desired.

In the final stage, the trimethylsilyl protecting group and the ketal protecting groups are removed by treatment with the appropriate deblocking reagents to give the desired 10-(2-propynyl)estr-4-ene-3,17-dione (7). That is, acid treatment removes the ketal protecting groups and base treatment removes the trimethylsilyl protecting group and, during the course of these procedures, dehydration takes place with removal of the 5-hydroxy group and introduction of a double bond at the 4-position so that a combination of the two treatments, in either order, serves to give the desired product. Thus, for example, in step (v) the bisgemdimethyl ketal (5) is deprotected by stirring with a strong acid, such as, for example, p-toluenesulfonic acid (PTSA) in acetone to yield the silyl propyne alcohol (6). This compound is then dehydrated in step (vi), and the silyl group is removed to yield 10-(2-propynyl)estr-4-ene-3,17-dione (7) by treating with methanolic sodium hydroxide at room temperature for 1–24 hours. Alternatively, the silyl protecting group can be removed first followed by removal of the ketal protecting groups. Thus, the trimethylsilyl group can be removed from the bisgemdimethyl ketal (5) in step (vii) by treating the ketal with base, such as, for example, NaOMe in tetrahydrofuran to give (8) followed by subsequent addition of a strong protic acid, such as concentrated sulfuric acid, in step (viii) to yield the desired 10-(2-propynyl)estr-4-ene-3,17-dione (7). In either case, the two procedures can be combined into a single step as shown by step (v'). Preferably, the bisgemdimethyl ketal (5) is treated with base first rather than last because, in the latter situation, the product 10-(2-propynyl)estr-4-ene-3,17-dione (7) may be exposed to base over an extended period of time and it is not stable under such conditions. Thus, use of base in the final step may result in a reduction in the yield of the product, particularly when the procedure is carried out on a large scale.

As far as the improved process for the synthesis of δ-unsaturated alkanols is concerned, this reaction is illustrated by step (iv) above. The reaction is illustrated for a 2-propynyl organometallic compound and a particular steroid epoxide but a 2-propenyl organometallic compound can be used instead of the propynyl compound and other epoxides can be used instead of the indicated epoxide.

The following examples are presented to illustrate the present invention. They are not to be construed as limiting it in any way.

EXAMPLE 1A 3,3,17,17-Bis (2,2-dimethyltrimethylenedioxy) -19-norandrost-5(10)-ene (2) (Step i)

Ketalization of Δ5(10)-Norandrostene-3,17-dione with Triethyl Orthoformate and 2,2-Dimethyl-1,3-propanediol in Toluene.

19-Norandrost-5(10)-ene-3,17-dione (NAD) (100 grams, 0.368 moles), 2,2-dimethyl-1,3-propandiol (150 grams, 1.44 moles) and triethyl orthoformate (160 grams, 1.1 moles) were mixed in toluene (1 liter) and cooled to 0°–4° C. To this stirred mixture, p-toluenesulfonic acid monohydrate (0.25 grams) was added. Stirring was continued until all the solid had dissolved and the reaction was held at 4° C. for 72 hours. The reaction was treated with a saturated solution of sodium carbonate (100 ml) and ethyl ether (250 ml). The organic layer was separated and washed five times with water (100 ml portions). The organic layer was dried over MgSO$_4$, filtered and the solvent removed under reduced pressure. The residue was covered with 200 ml of methanol and stored at 0°–4° C. overnight. The solid was collected and washed with cold methanol, yielding 135 grams of 3,3,17,17-bis(2, 2-dimethyltrimethylenedioxy)-19-norandrost-5(10)-ene.

EXAMPLE 1B

Ketalization of Δ5(10)-Norandrostene-3,17-dione with Trimethyl Orthoformate and 2,2-Dimethyl-1,3-propanediol in Methanol.

p-Toluenesulfonic acid (0.317 g) was added at 0° C. to a solution of Δ5(10)-norandrosten-3,17-dione (10 g, 37 mmol), 2,2-dimethyl-1,3-propanediol (15 g, 144 mmol), and trimethyl orthoformate (11.46 g, 108 mmol) in methanol (100 ml). The reaction became homogeneous after 20 minutes and was allowed to stand unstirred at 4° C. overnight. Standard GC analysis indicated the major products were methyl enol ether at C-3 with the cyclic ketal at C-17 (structure was derived by coinjection with an authentic sample, Akzo) and the expected bisketal. After stirring at room temperature for an additional two days, the bisketal crystallized from solution. However, the methyl enol ether was still present in substantial amounts (>25 area %). The catalyst was quenched with pyridine (1 ml), the mixture was filtered, and the solid was washed three times with cold methanol, to which several drops of pyridine had been added. After vacuum drying (60° C., 18 mm Hg), a 57% yield (9.37 g) of bisketal [3,3,17,17-bis(2,2-dimethyltrimethylenedioxy)-19-norandrost-5(10)-ene] was obtained (84 GC area %).

EXAMPLE 1C

Ketalization of Δ5(10)-Norandrostene-3,17-dione with Ramped Temperature Profile

Δ5(10)-Norandrostene-3,17-dione (NAD) (10 g, 37 mmol) and toluene (100 ml) were mixed in a stirred 250 ml flask under one atmosphere of nitrogen at 0° C. The NAD did not totally dissolve. Triethyl orthoformate (16 g, 108 mmol) and 2,2-dimethyl-1,3-propanediol (15 g, 144 mmol) were added to the heterogeneous mixture. Upon addition of p-toluenesulfonic acid (0.0317 g, 0.0036 equivalents) an endothermic reaction was noted and in about 15 minutes, the reaction mixture became homogenous. Samples (50 μl) were removed and quenched at 0° C. into a vial containing 1 ml of cyclohexane and 1 ml of saturated aqueous sodium bicarbonate solution. GC analysis on 5 μl of the cyclohexane layer was used to follow the reaction. After 6 hours, all the Δ5(10)-norandrostene-3,17-dione and intermediate 3-enol ethers were converted to the corresponding 3-ketal compound. The temperature of the reaction mixture was increased to 22° C. and the reaction was stirred for an additional 18 hours. The reaction was poured into cold aqueous saturated sodium bicarbonate, extracted with ethyl acetate (3×100 ml), dried over Na$_2$SO$_4$, and concentrated to a yellow oil by rotary evaporation. The oil was covered with methanol (50 ml) and the solids that formed were allowed to stand overnight at 4° C. After filtration, washing with cold methanol (3×25 ml) and drying, 18.81 g (84% yield, 96 area % by GC) of the bisketal [3,3,17,17-bis(2,2-dimethyltrimethylenedioxy)-19-norandrost-5(10)-ene] was obtained.

EXAMPLE 1D

Effect of Catalyst Levels on the Low Temperature Ketalization of Δ5(10)-Norandrostene-3,17-dione.

In this series of experiments, the catalyst loading was varied from 0.36 mole % to 3.60 mole % based on Δ5(10)-norandrostene-3,17-dione. Five experiments were run under standard conditions in which p-toluenesulfonic acid (0.317 g, 0.0793 g, 0.1585 g, 0.2378 g, and 0.3170 g, or 0.36, 0.9, 1.8, 2.7, and 3.6 mol %, respectively) was added to a solution of Δ5(10)-norandrostene-3,17-dione (10 g, 37 mmol), 2,2-dimethyl 1,3-propanediol (15 g, 144 mmol), and trimethyl orthoformate (11.46 g, 108 mmol) in methanol (100 ml) at 0° C. Samples (50 μl) were removed and quenched at 0° C. into a vial containing 1 ml of cyclohexane and 1 ml of aqueous saturated sodium bicarbonate solution. GC analysis was carried out on 5 μl of the cyclohexane layer for Δ5(10)-norandrostene-3,17-dione. Each reaction was isolated as described above and the following yields for the bisketal [3,3,17,17-bis(2,2-dimethyltrimethylenedioxy)-19- norandrost-5(10)-ene] were obtained: 83%, 80%, 74%, 57%, and 84%, respectively.

EXAMPLE 1E

Ketalization of Δ5(10)-Norandrostene-3,17-dione in Ethanol.

This procedure provides a solvent medium from which the product crystallizes as it is formed: p-Toluenesulfonic acid (0.317 g, 0.36 mol %) was added at 0° C. to a solution of Δ5(10)-norandrostene-3,17-dione (100 g, 370 mmol), 2,2-dimethyl-1,3-propanediol (150 g, 1.44 mol), and triethyl orthoformate (213.3 g, 1.44 mol) in ethanol (400 ml). The reaction mixture was held at 4° C. After 72 hours, the heterogeneous reaction was quenched with triethylamine (1 ml), filtered while cold, and washed with a total of 100 ml cold ethanol which had been treated with 0.25 ml triethylamine. Vacuum drying (50° C.) gave 130.2 g of bisketal (m.p. 148°–150° C.). A similar run was done with a higher catalyst loading (0.63 g, 0.9 mol %). The product began to crystallize after 6 hours and the reaction was worked up after 24 hours. The isolated yield and the physical properties of the bisketal [3,3,17,17-bis(2,2-dimethyltrimethylenedioxy)-19-norandrost-5(10)-ene] were essentially identical to that reported above.

EXAMPLE 1F

Large Scale Ketalization of Δ5(10)-Norandrostene-3,17-dione in Ethanol.

p-Toluenesulfonic acid (6.28 g, 0.9 mol % was added at 0° C. to a solution of Δ5(10)- norandrostene-3,17-dione (1000 g, 3.70 mol), 2,2-dimethyl-1,3-propanediol (1530 g, 14.4 mol), and triethyl orthoformate (2176.3 g, 14.4 mol) in ethanol (6.5 L, grade 3C). A cooling bath set to 0° C. was used to maintain a constant temperature. However, unlike the toluene runs, the ketalization in ethanol was exothermic, and the bath temperature crept up to 5° C. during the first hour. After 24 hours, the heterogeneous reaction was quenched with triethylamine (30 ml), filtered while cold, and washed with cold ethanol:water (50:50) to which 1 ml of triethylamine was added (2×500 ml). Vacuum drying (30° C., 72 hours) gave 1640 g (theoretical yield: 1632 g) of the bisketal which was 95% area by GC analysis. NMR analysis showed that water remained in the sample (estimated amount: 51 g). The sample was dried again (50° C., 2 days) to give 1545 g of the bisketal [3,3,17,17-bis(2,2-dimethyltrimethylenedioxy)-19-norandrost-5(10)-ene] (95% yield) with a melting point of 149°–150° C.

EXAMPLE 2A (5α,10α)-5,10-Epoxy-3,3,17,17-bis(2,2-dimethyltrimethylenedioxy)-19-norandrostane (4) (Steps ii and iii)

3,3,17,17-Bis(2,2-dimethyltrimethylenedioxy)-19-norandrost-5(10)-ene (0.66 grams, 0.0015 mole) was dissolved in DMF (10 ml) and THF (2 ml) and added to water (1.5 ml). Magnesium oxide (0.06 grams, 0.0015 mole) and freshly recrystallized N-bromosuccinimide (NBS) (0.8 grams, 0.0045 mole) were combined and then divided into 8 equal batches. Each batch was added to the reaction at 15 minute intervals while maintaining the temperature at 20° C. with external cooling. The resulting reaction was stirred for 0.5 hour, then diluted with water (15 ml). The resulting precipitate was filtered, dried, and taken up in ethyl acetate (50 ml). The ethyl acetate was dried ($Na_2SO_4$) and evaporated to yield the bromohydrin (3) (weight: 0.817 grams) as a white solid. The bromohydrin (3) (0.81 grams, 0.0015 mole) and potassium tertbutoxide (0.34 grams, 0.003 mole) were added to THF (10 ml) and stirred at room temperature for 1 hour. The resulting mixture was poured into water (50 ml) and extracted with ethyl acetate (2×75 ml). The ethyl acetate extracts were combined and washed with brine (75 ml). The resulting solution was dried ($Na_2SO_4$) and evaporated to a residue. The residue was then crystallized from methanol to yield 0.54 grams of white crystalline (5α,10α)5,10-epoxy-3,17-bis(2,2-dimethyltrimethylenedioxy)androstane.

EXAMPLE 2B

Alternate method of preparing (5α,10α)-5,10-epoxy-3,17-bis (2,2-dimethyltrimethylenedioxy)-19-norandrostane (4) from 3,3,17,17-bis ( 2,2-dimethyltrimethylenedioxy)-19-norandrost-5(10)-ene (2):

Preparation of the Bromohydrin (3) from the Bisgemdimethyldioxan (2).

To a three necked flask equipped with a bottom drain, thermometer, nitrogen inlet, and addition funnel, was added 3,3,17,17-bis(2,2-dimethyltrimethylenedioxy)-19-norandrost-5(10)-ene (2) (150 g, 337 mmol), THF (400 ml), and 0.05M $KH_2PO_4$ buffer at pH 8 (300 ml). N-Bromsuccinimide (NBS) (75 g, 422 mmol) was dissolved in a mixture of THF (1 L) and 0.05M $KH_2PO_4$ buffer at pH 8 (250 ml) and added dropwise to the steroid solution while maintaining the reaction mixture temperature at 10°–25° C. Complete conversion of the bisgemdimethyldioxan (2) to the bromohydrin (3) was observed within 15 minutes of NBS addition, at which point the bromohydrin had crystallized from solution. Work-up A: $Na_2SO_3$ (11.25 g, 84.3 mmol) was dissolved in water 100 ml, and added to the heterogeneous reaction mixture. Filtration of the solution provided the solid bromohydrin (3) in high yield. Work-up B: The excess NBS was quenched by the addition of $Na_2SO_3$ (11.25 g, 84.3 mmol) dissolved in saturated sodium chloride solution (500 ml). The precipitated bromohydrin dissolved and a phase separation occured. The aqueous layer was removed through the bottom drain leaving a homogeneous solution of the bromohydrin (3) in THF. This solution can be directly converted to the epoxide (4) described below.

Preparation of the Epoxide (4) from the Bromohydrin (3).

To the THF solution of bromohydrin (3) (from Work-up B, above) was added (2.5 equivalents per equivalent of bromohydrin) MSA-1-OH Dowex® ion exchange beads in the strong base form. The solution was stirred at room temperature for 18–24 hours, at which time the conversion of the bromohydrin to the epoxide was complete. After removal of the beads by filtration, the epoxide solution was dried by any of several methods including azeotropic distillation of THF and water, or by the addition of a drying agent such as $MgSO_4$, $CaSO_4$, or $Na_2SO_4$. The dry solution was carried into the next step, the cuprate addition, without further manipulation. Alternatively, the epoxide (4) was isolated in greater than 95% yield by concentration of the dried solution (80% pure by LC assay). The material could be recrystallized from methanol, or preferably acetone:water (90:10) in 70–80% isolated yield. This procedure may also be used with the substitution of other equivalents for base, such as benzyltrimethyl-ammonium hydroxide, NaOMe, NaOH, or KOH.

This epoxide is then further reacted with the cuprate reagent as described in Example 3C below.

EXAMPLE 3A

10-[3-(Trimethylsilyl)-2-propynyl]-3,3,17,17-bis (2,2-dimethyltrimethylenedioxy)-19-norandrostan-5-ol (5) (Step iv)

[Method 1 —Utilizing copper(I) bromide]. To an oven-dried flask equipped with septa and $N_2$ inlet was added 1-(trimethylsilyl)propyne (0.90 ml, 0.0061 mole) in anhydrous ether (3.0 ml). The reaction was cooled to −5° C., and 1.14M n-BuLi (5.79 ml, 0.066 mole) was added. The reaction was stirred at this temperature, under $N_2$, for 10 minutes.

To a separate oven-dried 3-necked flask equipped with two addition funnels, septa, and $N_2$ inlet, copper(I) bromide-dimethylsulphide complex was added under an inert atmosphere. One addition funnel was charged with (trimethylsilyl)C≡C—$CH_2$Li solution.

To the copper bromide-dimethylsulphide complex, was added dimethylsulphide (0.3 ml) and anhydrous ether (3.0 ml). The mixture was cooled to −15° C. to 0° C. (ethylene glycol, $CO_2$) and dropwise addition of propyne solution was begun. The mixture turned black almost immediately. Stirring and temperature were maintained 10 minutes after addition was completed. Dropwise addition of (5α,10α)-5,10-epoxy-3,17-bis(2,2-dimethyltrimethylenedioxy)-19-norandrostane (0.46 grams, 0.001 mole) in ether (3 ml) was begun, with the temperature allowed to warm up to 0° C. The reaction was stirred at this temperature until TLC (30% EtOAc:Hex) indicated the reaction was complete. The reaction was then allowed to warm to room temperature. Silica gel (1 gm) was added and solvent removed in vacuo. The preabsorbed silica gel was placed on a silica gel plug and the plug was washed with excess EtOAc (2×100 ml). The brown filtrate was washed with 10% $NH_4OH$/saturated $NH_4Cl$ (10 ml), followed by NaCl (saturated). The organic layer was dried ($MgSO_4$), then the solvent was stripped leaving a brown residue. Isopropanol was added and the mixture was heated until it became a homogeneous solution. The isopropanol solution was reduced to half its original volume and left for crystallization. Flash chromatography (30% EtOAc:Hex) yielded 0.34 gram of 10-[3-(trimethylsilyl)-2-propynyl]-3,17-bis(2,2-dimethyltrimethylenedioxy)-19-norandrostan-5-ol as cream colored crystals from three crops (76% yield).

EXAMPLE 3B

10-[3-(Trimethylsilyl),2-propynyl]-3,3,17,17-bis (2,2-dimethyltrimethylenedioxy)-19-norandrostan-5-ol (5) (Step iv)

[Method 2 —Utilizing copper cyanide]. To a 3-necked flask equipped with a thermometer, $N_2$ inlet, and septa was added 1-(trimethylsilyl)propyne (0.965 ml, 0.00652 mole) in dry ether (10 ml). The reaction was cooled to 0° C. and 1.14M n-BuLi (5.7 ml, 0.00652 mole) was added, keeping the temperature below 2° C. for 0.5 hour. Copper cyanide (0.29 grams, 0.00326 mole) was added in one portion. The reaction was stirred for 0.5 hour at 0° C., with an orange solution being formed. (5α,10α)-5,10-Epoxy-3,3,17,17-bis(2,2-dimethyltrimethylenedioxy)-19-norandrostane (0.5 grams, 0.00109 mol) was added in one portion and stirred overnight under $N_2$ at 0° C. The resulting dark solution was quenched with 10% $NH_4OH$/saturated $NH_4Cl$ (20 ml) and stirred for 1 hour to remove the dark color. The organic layer was extracted with ethyl acetate (50 ml), dried ($Na_2SO_4$), and evaporated to give 0.61 grams of pure, straw colored, 10-[3'(trimethylsilyl)-2-propynyl]-3,17-bis(2,2-dimethyltrimethylenedioxy)-19-norandrostan-5-ol (5) (98% yield).

EXAMPLE 3C

10-[3-(Trimethylsilyl)-2-propynyl]-3,3,17,17-bis (2,2-dimethyltrimethylenedioxy)-19-norandrostan-5-ol (5) (Step iv)

[Method 3 —Utilizing lithium methyl-2-thienylcuprate]. To a 3-necked flask equipped with a septum, a thermometer, nitrogen inlet, and addition funnel, was added 1-(trimethylsilyl)propyne (1.68 grams, 15 mmole) and tetrahydrofuran (5 ml). n-Butyl lithium (9.74 ml, 1.6M, 15 mmole) was transferred to the addition funnel and added dropwise to the solution while maintaining the temperature at 0° C. Lithium methyl-2-thienylcuprate (21.4 ml, 0.7M in THF and toluene solution, 15 mmole) (Lithco Corp.), was then added dropwise to the above solution. The mixed higher order cuprate solution was stirred for 5 minutes at 0° C. The epoxide (4) (2.30 grams, 5 mmole) was dissolved in THF (3 ml) and toluene (5 ml) and added to the cuprate. After 4 hours the epoxide (4) was reacted. The product was isolated by quenching the excess organometallic reagent with ammonium hydroxide (10%) in saturated ammonium chloride solution. Solids were removed by filtration. Toluene (20 ml) was added and the layers separated. The organic layer was washed 3 times with 50 ml ammonium hydroxide (10%) in saturated ammonium chloride solution and dried over sodium sulfate. Concentration resulted in 2.70 grams of the crude product, 10-[3-(trimethylsilyl)-2-propynyl]-3,3,17,17-bis(2,2-dimethyltrimethylenedioxy)-19-norandrostan-5-ol (5) (93% yield, 80% pure by LC analysis).

EXAMPLE 3D

10-[3-(Trimethylsilyl)-2-propynyl]-3,3,17,17-bis (2,2-dimethyltrimethylenedioxy)-19-norandrostan-5-ol (5) (Step iv)

To a three-necked flask equipped with a septum, a thermometer, nitrogen inlet, and an addition funnel, was added 1-(trimethylsilyl)propyne (TMSP, 20.0 g, 150 mmol) and tetrahydrofuran (50 mL). n-Butyl lithium (97.4 mL, 1.6M, 150 mmol) was transferred to the addition funnel and added dropwise to the TMSP solution. The addition rate of the n-butyl lithium was adjusted to maintain the temperature of the reaction mixture at about 4° C. After the addition was complete (20 min), the TMSP solution was stirred at 4° C. for 15–30 min. Lithium methyl-2-thienylcuprate (8.0 mL, 0.65M in THF and toluene solution, 5 mmol) was added dropwise to the above solution. A solution of (5α,10α)-5, 10-epoxy-3,3,17,17-bis(2,2-dimethyltrimethylenedioxy)-19-norandrostane (23.0 g, 50 mmol), THF (30 mL) and toluene (50 mL) was added to the above solution via cannula. After 18 hours, TLC analysis (Hexane:ethyl acetate, 90:10) indicated that the epoxide had completely reacted. The reaction was quenched with a solution of ammonium hydroxide (30 wt%) saturated with ammonium chloride (25 mL) at 0° C. and stirred for 20 min. The insoluble lithium and copper salts were removed by filtration through celite (20 g). The salts were washed with THF (3×40 mL). The clear yellow solution was concentrated by rotary evaporation at 40° C. The residue was treated with 25 mL methanol. The white solids were filtered, washed with cold methanol (3×15 mL), and dried overnight at 40° C. (22 mm Hg) to give 20.78 g of 10-[3-(trimethylsilyl)-2-propynyl]-3,3,17,17-bis(2,2-dimethyltrimethylenedioxy)-19-norandrostan-5-ol (73% yield, >100 wt%).

EXAMPLE 3E

10-[3-(Timethylsilyl)-2-propynyl]-3,3,17,17-bis (2,2-dimethyltrimethylenedioxy)-19-norandrostan-5-ol (5) (Step iv)

To a three-necked flask equipped with a septum, a thermometer, nitrogen inlet, and an addition funnel, was added 1-(trimethylsilyl)propyne (TMSP, 1.68 g, 15 mmol) and tetrahydrofuran (5 mL). n-Butyl lithium (9.74 mL, 1.6M, 15 mmol) was transferred to the addition funnel and added dropwise to the TMSP solution. The addition rate of the n-butyl lithium was adjusted to maintain the temperature of the reaction mixture at about 4° C. After the addition was complete, the solution was stirred at 4° C. for about 15 minutes. Lithium di-2-thienylcuprate (21.4 mL, 0.7M in THF and toluene, 15 mmol) was added dropwise to the solution and the solution of cuprate was stirred for 5 min at 0° C. A solution of ($5\alpha,10\alpha$)-5,10-epoxy-3,3,17,17-bis(2,2-dimethyltrimethylenedioxy)-19-norandrostane (2.30 g, 5 mmol), dissolved in THF (3 mL) and toluene (5 mL), was added to the cuprate solution. After 4 hours, TLC analysis (hexane:ethyl acetate, 90:10) indicated that the epoxide had completely reacted. The reaction mixture was quenched and isolated as described above to give crude 10-[3-(trimethylsilyl)-2-propynyl]-3,3,17,17-bis(2,2-dimethyltrimethylenedioxy)-19-norandrostan-5-ol, in an estimated yield of 80%.

EXAMPLE 4A 10-(2-Propynyl)estr-4-ene-3,17-dione (7)

10-[3-(Trimethylsilyl)-2-propynyl]-3,3,17,17-bis(2,2-dimethyltrimethylenedioxy)-19-norandrostan-5-ol (5) (0.2 grams, 0.00035 mole) was dissolved in acetone (20 ml) and p-toluenesulfonic acid (PTSA) monohydrate (0.02 grams) was added. The resulting clear solution was stirred for 2 hours then evaporated to an off-white powder. The powder was dissolved in 5% NaOH methanol (20 ml) and stirred at room temperature for 1 hour. The reaction was poured into ice cold 0.01M hydrochloric acid (25 ml), saturated brine (25 ml), and dried (MgSO$_4$). Evaporation and recrystallization from methanol yielded 0.085 grams (78% yield) of 10-(2-propynyl)-estr-4-ene-3,17-dione (7) as straw colored crystals.

EXAMPLE 4B

10-[3-(Trimethylsilyl)-2-propynyl]-5-hydroxyandrostane-3,17-dione (6) (Step v)

10-[3-(Trimethylsilyl)-2-propynyl]-3,3,17,17-bis(2,2-dimethyltrimethylenedioxy)-19-norandrostan-5-ol (5) (0.37 grams, 0.00078 mole), p-toluenesulfonic acid (PTSA) monohydrate (0.09 grams) in acetone were mixed and stirred at room temperature for 1 hour. The solution was evaporated to a residue, which was taken up in ethyl acetate (50 ml) and washed with saturated sodium bicarbonate (50 ml). The ethyl acetate layer was dried (Na$_2$SO$_4$) and evaporated to a white solid of 10-[3-(trimethylsilyl)-2-propynyl]-5-hydroxyandrostane-3,17-dione (6) (wt: 0.33 grams). The solid was analytically pure without any further purification.

10-(2-Propynyl)estr-4-ene-3,17-dione (7) (Step vi)

A 5% solution of NaOH pellets in methanol was formed and 25 ml added to 10-[3-(trimethylsilyl)-2-propynyl]-5-hydroxyandrostane-3,17-dione (0.3 grams, 0.00075 mole). The reaction was stirred for 1 hour, then poured into water (200 ml), and extracted with ethyl acetate (4×50 ml). The organic fractions were combined, dried (Na$_2$SO$_4$), and evaporated to a residue. Recrystallization from methanol yielded 0.21 grams (90.3% yield) of 10-(2-propynyl)estr-4-ene-3,17-dione (7).

EXAMPLE 4C

10-[3-(Trimethylsilyl)1,2,propynyl]-5-hydroxyandrostane-3,17-dione (6) (Step v)

[Continuation of Method 1, Example 3A]. A cuprate reaction was carried out without purification of the resulting intermediate, 10-[3-(trimethylsilyl)-2-propynyl]-3,3,17,17-bis(2,2-dimethyltrimethylenedioxy)-19-norandrostan-5-ol. The reaction was carried out exactly as described in Example 3A, up to the work up. The reaction was quenched with 10% NH$_4$OH/saturated NH$_4$Cl (20 ml) and the heterogeneous mixture filtered to remove black sludge-like material. The filtrate was separated into two layers. The organic layer was washed with additional 10% NH$_4$OH/saturated NH$_4$Cl (2×10 ml), H$_2$O (15 ml), then saturated brine (15 ml). The organic layer was dried (MgSO$_4$) and evaporated to a brown residue. The residue was taken up in acetone (20 ml), and p-toluenesulfonic acid (PTSA) monohydrate (0.05 grams) was added. The reaction was stirred at room temperature for 2 hours then evaporated to a light brown residue. The residue was dissolved in EtOAc (100 ml) and washed with saturated NaHCO$_3$ (20 ml). The aqueous layer was further washed with EtOAc (4×50 ml) and the extracts combined, dried (MgSO$_4$), and evaporated to a light brown solid. Crystallization from MeOH (2 ml) with cooling to −20° C. yielded 0.31 grams of 10[3-(trimethylsilyl)-2-propynyl]-5-hydroxyandrostan-3,17-dione (6) (78% yield) as an off-white solid. The trimethylsilyl group is then removed by treatment with base according to the procedure described in the second paragraph of Example 4B.

EXAMPLE 4D 10-(2-Propynyl)estr-4-ene-3,17-dione (7) (Steps vii and viii)

10-[3-(Trimethylsilyl)-2-propynyl]-3,17-bis(2,2-dimethyltrimethylenedioxy)-19-norandrostan-5-ol (5) (5.00g, 8.73 mmoles) and THF (50 mL) were combined in a 100-mL, 4-necked, jacketed, straight walled reaction flask; equipped with an overhead mechanical stirrer, N$_2$ oil bubbler, internal K-thermocouple connected to a Fluke 51 K/J thermometer and septum. The stirred solution was placed under N$_2$ and 25 wt % NaOMe/MeOH (2.0 mL, ca. 0.473 g, 8.75 mmoles of NaOME) was added via syringe during 15 seconds. The internal temperature dropped ~1° C. and the reaction mixture became cloudy and pale yellow. The reaction mixture was heated to 49°±1° C. and stirred under N$_2$ for 2 ½ hours. After cooling to 11° to 12° C., concentrated H$_2$SO$_4$ (6.0 g) was added in portions and the acidified reaction mixture was stirred an additional 4 hours at 25°±2° C. The reaction mixture was cooled to 3° to 5° C. with stirring and water (100 mL at room temperature) was added via syringe during 25 minutes at such a rate that the reaction temperature did not exceed 10° C. The resulting slurry was stirred at 3° to 5° C. for an additional ½ hour after which the solids were collected by vacuum filtration. The residual solids in the flask were washed out with water (2×2.5 mL), and the washings pulled through the filter. The wet cake (5.81 g) was transferred to a 50 mL round-bottom flask equipped with a magnetic stir bar, reflux condensor and $N_2$ oil bubbler. Ethanol (30 mL) was added and the stirred slurry was warmed to near reflux. The clear yellow solution was filtered and allowed to cool to room temperature with stirring overnight. After filtration, the wet cake was washed with EtOH (10 mL) and dried (27 mm/45° C./2 hr) to afford 1.62 g (74.6%) of 10-(2-propynyl)estr-4-ene-3,17-dione as a white solid. Concentration of the mother liquors afforded 0.42 g of 10-(2-propynyl)estr-4-ene-3,17-dione as a yellow solid. The THF/water liquors from the initial precipitation step yielded an additional 0.11 g of 10-(2-propynyl)estr-4-ene-3,17-dione on standing.

What is claimed is:

1. A process for the preparation of 10-(2-propynyl)-estr-4-ene-3, 17-dione which comprises:

a) reacting (5S,10S)-5, 10-epoxy-3,3,17,17-bis(2,2-dimethyltrimethylenedioxy)-19-norandrostane with a mixed higher order trialkylsilyl protected 2-propynyl copper dilithium reagent having three organic substituents, one of which is trimethylsilyl, with the others selected from the group consisting of thienyl and methyl, in tetrahydrofuran to yield the bisgemdimethyl ketal, 10-[3-(trialkylsilyl)-2-propynyl]-3,3,17,17-bis(2, 2-dimethyltrimethylenedioxy)-19-norandrostan-5-ol, and b) reacting 10-[3-(trialkylsilyl)-2-propynyl]-3,3,17,17-bis(2,2-dimethyltrimethylenedioxy)-19-norandrostan-5-ol with base and with acid to yield 10-(2-propynyl)-estr-4-ene-3, 17-dione.

2. A process according to claim 1 wherein the cuprate reacted to form the bisgemdimethyl ketal is dilithium [3-(trimethylsilyl)-2-propynyl]methyl-2-thienylcuprate or dilithium[3-(trimethylsilyl)-2-propynyl]di-2-thienyl-cuprate.

\* \* \* \* \*

UNITED STATES PATENT AND TRADEMARK OFFICE
CERTIFICATE OF CORRECTION

PATENT NO. : 5,516,922

DATED : May 14, 1996

INVENTOR(S) : Cynthia L. Rand

It is certified that error appears in the above-indentified patent and that said Letters Patent is hereby corrected as shown below:

Column 5, Line 5 patent reads: "A5" and should read --$\Delta^5$--.

Column 12, Line 7 patent reads: " [3' "and should read -- [3- --.

Column 14, Line 15 patent reads: ",2, propynyl" and should read -- -2-propynyl --.

Column 16, Line 1 patent reads: "(58, 108)" and should read -- $(5\partial, 10\partial)$ --.

Signed and Sealed this

Tenth Day of June, 1997

BRUCE LEHMAN

Attest:

Attesting Officer    Commissioner of Patents and Trademarks